United States Patent [19]

Kanno et al.

[11] Patent Number: 5,691,277

[45] Date of Patent: Nov. 25, 1997

[54] 2-(UNSUBSTITUTED OR SUBSTITUTED) (BENZYLOXY OR PHENOXY)-4-SUBSTITUTED-6-(META-SUBSTITUTED PHENOXY)PYRIDINE, PROCESS FOR PRODUCING THE SAME, AND HERBICIDAL COMPOSITION

[75] Inventors: Hisashi Kanno; Youichi Kanda; Susumu Shimizu; Yoshikazu Kubota; Tsutomu Sato; Masato Arahira, all of Iwaki, Japan

[73] Assignee: Kureha Kagaku Kogyo Kabushiki Kaisha, Japan

[21] Appl. No.: 501,842

[22] Filed: Jul. 13, 1995

[30] Foreign Application Priority Data

| Jul. 14, 1994 | [JP] | Japan | 6-185367 |
| Jul. 20, 1994 | [JP] | Japan | 6-190085 |
| Feb. 4, 1995 | [JP] | Japan | 7-039080 |
| Feb. 4, 1995 | [JP] | Japan | 7-039081 |

[51] Int. Cl.$^6$ .......................... C07D 213/69; A01N 43/40
[52] U.S. Cl. .......................... 504/244; 504/256; 546/296
[58] Field of Search .......................... 504/244, 256; 546/296

[56] References Cited

U.S. PATENT DOCUMENTS

| 3,535,328 | 10/1970 | Zielinski | 546/275 |
| 3,687,959 | 8/1972 | Zielinski | 546/291 |
| 4,898,608 | 2/1990 | Sasse et al. | 504/257 |
| 5,152,825 | 10/1992 | Gilkerson et al. | 504/255 |
| 5,318,946 | 6/1994 | Condon et al. | 6/244 |
| 5,374,604 | 12/1994 | Kleeman et al. | 504/130 |

FOREIGN PATENT DOCUMENTS

| 0572093 | 12/1993 | European Pat. Off. |
| 572093 | 12/1993 | European Pat. Off. |

OTHER PUBLICATIONS

Chemical Abstract, vol. 120, 1994, P191543h.

*Primary Examiner*—C. Warren Ivy
*Assistant Examiner*—Lyman H. Smith
*Attorney, Agent, or Firm*—Parkhurst, Wendel & Burr, L.L.P.

[57] ABSTRACT

A 2-(unsubstituted or substituted) (benzyloxy or phenoxy)-4-substituted-6-(meta-substituted phenoxy)pyridine represented by the formula (I):

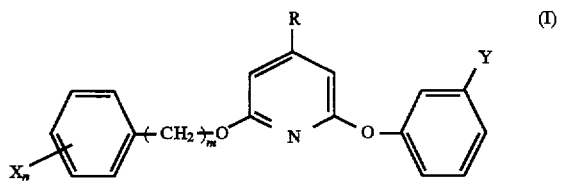

wherein R represents $C_1$–$C_4$ alkoxy or cyano;

each X, which may be identical or different if n is greater than 1, represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkythio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5, which is useful as a herbicide.

6 Claims, No Drawings

2-(UNSUBSTITUTED OR SUBSTITUTED) (BENZYLOXY OR PHENOXY)-4-SUBSTITUTED-6-(META-SUBSTITUTED PHENOXY)PYRIDINE, PROCESS FOR PRODUCING THE SAME, AND HERBICIDAL COMPOSITION

BACKGROUND OF THE INVENTION

The present invention relates to a novel 2-(unsubstituted or substituted)(benzyloxy or phenoxy)-4-substituted-6-(meta-substituted phenoxy)pyridine, a process for producing the compound and a herbicidal composition containing the compound as an active ingredient.

Some 2-(unsubstituted or substituted) (benzyloxy or phenoxy)-4-substituted-6-(meta-substituted phenoxy) pyridines which exhibit herbicidal activity have been disclosed in EP 572093 A. Among 2-benzyloxypyridine derivatives represented by the general formula disclosed in the U.S. Pat. No. 3,535,328, some have been found to have herbicidal activity.

Although various herbicides including the above have been proposed, it has been still demanded a herbicide having superior herbicidal activity, such as a reliable herbicidal effect at such a low application dose that the residual amount in the environment advantageously decreases, good selectivity between crops and weeds regardless of environmental condition changes, and low phytotoxicity to the succeeding crop cultivated in a double cropping system.

The present invention has been achieved for the purpose of meeting the existing demands as set forth above. The object of the present invention is, therefore, to provide a novel compound having herbictdal activity, a process for producing the compound and a novel herbicidal composinion containing the compound as an active ingredient.

The present inventors, with a view to discover novel industrially useful pyridine derivatives, have conducted extensive researches on chemical structures and physiological activities on plants and found surprisingly. that the compounds which have alkoxy or cyano at the position 4 on the pyridine ring exhibit superior herbicidal activity when compared with the compounds (A) to (D) disclosed as preferred compounds in EP 572093 A or the compound (E) (Registry Number 153564-12-6 in Chem. Abstr.) which is not described in the publication but abstracted in the Chemical Abstracts [120, P 191543h(1994)] as a compound disclosed in the publication:

(A) 2,6-di(meta-trifluoromethylphenoxy)pyridine;

(B) 2,6-di(meta-trifluoromethylphenoxy)-4-methylmercaptopyridine;

(C) 2,6-di(meta-trifluoromethylphenoxy)-4-methylpyridine;

(D) 2-benzyloxy-6-(meta-trifluoromethylphenoxy)-pyridine;

(E) 4-chloro-2,6-di(meta-trifluoromethylphenoxy)-pyridine.

It has been thus found the novel 2-(unsubstituted or substituted) (benzyloxy or phenoxy)-4-substituted-6-(meta-substituted phenoxy)pyridine which is characterized by the particular combination of the substituents at the position 4 on the pyridine ring and the position 3 on the phenoxy ring and which has unexpected high herbicidal activity. The present invention was accomplished on the basis of this finding.

SUMMARY OF THE INVENTION

In a first aspect of the present invention, there is provided a 2-(unsubstituted or substituted)(benzyloxy or phenoxy)-4-substituted-6-(meta-substituted phenoxy)pyridine represented by the formula (I):

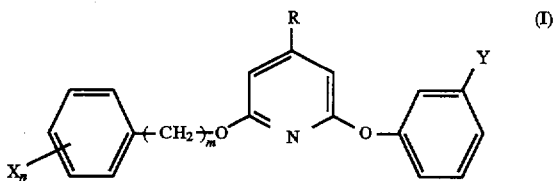

wherein R represents $C_1$–$C_4$ alkoxy or cyano; each X, which may be identical or different if n is greater than 1, represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5.

In a second aspect of the present invention, there is provided a process for producing a 2-(unsubstituted or substituted) (benzyloxy or phenoxy)-4-substituted-6-(meta-substituted phenoxy)pyridine of the formula (I):

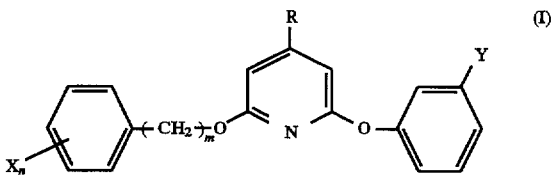

wherein R represents $C_1$–$C_4$ alkoxy or cyano;

each X, which may be identical or different if n is greater than 1, represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5, which process comprises reacting a 2-(unsubstituted or substituted) (benzyloxy or phenoxy)-4-substituted-6-halogenopyridine of the formula (II):

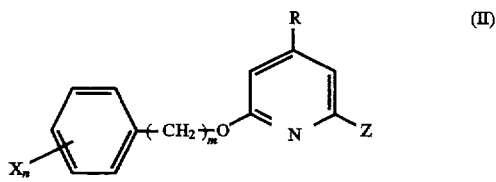

wherein R, X, m, and n are as defined above; and

Z represents a halogen, with a meta-substituted phenol of the formula (III):

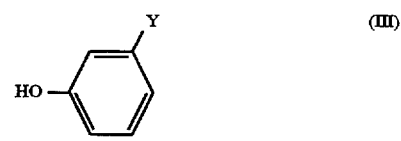

wherein Y is as defined above.

In a third aspect of the present invention, there is provided a process for producing a 2,6-di(meta-substituted phenoxy)-4-substituted-pyridine of the formula [(I'), corresponding to the compound (I) wherein X=Y (including the bonding position), n=1 and m=0]:

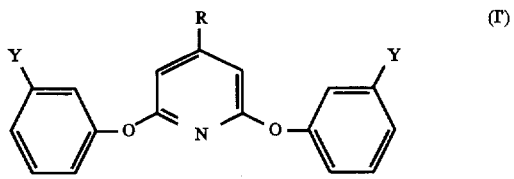

wherein R represents $C_1$–$C_4$ alkoxy or cyano; and

Y represents trifluoromethyl, difluoromethoxy, trifluoromethoxy, or trifluoromethylthio, which process comprises reacting a 2,6-dihalogeno-4-substituted-pyridine of the formula (IV):

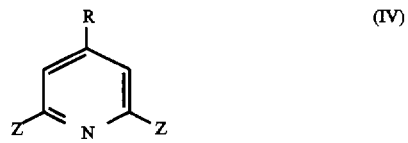

wherein R is as defined above and Z represents a halogen, with a meta-substituted phenol of the formula (III):

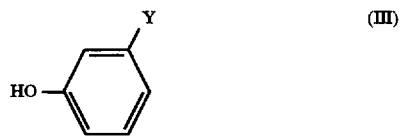

wherein Y is as defined above.

In a fourth aspect of the present invention, there is provided a herbicidal composition comprising a 2-(unsubstituted or substituted)(benzyloxy or phenoxy)-4-substituted-6-(meta-substituted phenoxy)pyridine of the formula (I):

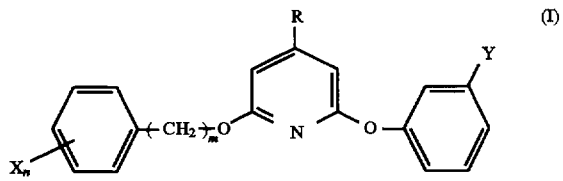

wherein R represents $C_1$–$C_4$ alkoxy or cyano;

each X, which may be identical or different if n is greater than 1, represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5, and an adjuvant.

DETAILED DESCRIPTION OF THE INVENTION

In the definition of each substituent in the 2-(unsubstituted or substituted)(benzyloxy or phenoxy)-4-substituted-6-(meta-substituted-phenoxy)pyridine of the formula (I), the substituents defined by the generic terms include preferred substituents as set forth below.

With respect to R, $C_1$–$C_4$ alkyloxy includes methoxy, ethoxy, and (1-methylethyl)oxy.

With respect to X, a halogen includes fluorine, chlorine, and bromine; $C_1$–$C_4$ alkyl includes methyl, ethyl, and 1-methylethyl; $C_1$–$C_4$ alkoxy includes methoxy, ethoxy and (1-methylethyl)oxy; $C_1$–$C_4$ haloalkoxy includes trifluoromethoxy and difluoromethoxy; $C_1$–$C_4$ haloalkyl includes trifluoromethyl; $C_1$–$C_4$ haloalkylthio includes trifluoromethythio; $C_3$–$C_5$ alkenyloxy includes allyloxy ($OCH_2CH=CH_2$), (2-methyl-2-propenyl)oxy ($OCH_2C(Me)=CH_2$), crotyloxy ($OCH_2CH=CHMe$), (3-methyl-2-butenyl)oxy ($OCH_2CH=C(Me)_2$), and (3-methyl-3-butenyl)oxy ($OCH_2CH_2C(Me)=CH_2$); and $C_3$–$C_5$ alkynyloxy includes (2-propynyl)oxy ($OCH_2CCH$).

Preferably, the substituents R, X and Y are as follows. R preferably represents methoxy or cyano. X preferably represents fluorine, chlorine, methyl, methoxy, or trifluoromethyl. Y preferably represents trifluoromethyl or trifluoromethoxy.

Preferably, n is 0 to 3.

Examples of the 2-(unsubstituted or substituted)(benzyloxy or phenoxy)-4-substituted-6-(meta-substituted phenoxy)pyridines of the formula (I) which has the combination of the preferred substituents and integers as described above are shown in the Table 1 below.

TABLE 1

| No. | R | $X_n$ [A)] | Y | m |
|---|---|---|---|---|
| I-1 | $OCH_3$ | Unsubstituted | $CF_3$ | 1 |
| I-2 | $OCH_3$ | Unsubstituted | $OCF_3$ | 1 |
| I-3 | CN | Unsubstituted | $CF_3$ | 1 |
| I-4 | $OCH_3$ | Unsubstituted | $SCF_3$ | 1 |
| I-5 | $OCH_3$ | 4-Cl | $CF_3$ | 1 |
| I-6 | $OCH_3$ | 3-Cl | $CF_3$ | 1 |
| I-7 | $OCH_3$ | 2-Cl | $CF_3$ | 1 |
| I-8 | $OCH_3$ | 2,4-$F_2$ | $CF_3$ | 1 |
| I-9 | $OCH_3$ | 4-F | $CF_3$ | 1 |
| I-10 | $OCH_3$ | 4-$OCH_3$ | $CF_3$ | 1 |
| I-11 | $OCH_3$ | 4-$CH_3$ | $CF_3$ | 1 |
| I-12 | $OCH_3$ | 2-F | $CF_3$ | 1 |
| I-13 | $OCH_3$ | 3-F | $CF_3$ | 1 |
| I-14 | $OCH_3$ | 2,6-$F_2$ | $CF_3$ | 1 |
| I-15 | $OCH_3$ | 3,5-$F_2$ | $CF_3$ | 1 |
| I-16 | $OCH_2CH_3$ | Unsubstituted | $CF_3$ | 1 |
| I-17 | $OCH_3$ | Unsubstituted | $OCHF_2$ | 1 |
| I-18 | $OCH_3$ | 3-$CF_3$ | $CF_3$ | 0 |
| I-19 | $OCH_3$ | 3-$SCF_3$ | $SCF_3$ | 0 |
| I-20 | $OCH_3$ | 3-$OCF_3$ | $OCF_3$ | 0 |
| I-21 | $OCH_3$ | 3-$OCHF_2$ | $OCHF_2$ | 0 |
| I-22 | $OCH_3$ | Unsubstituted | $CF_3$ | 0 |
| I-23 | CN | 3-$CF_3$ | $CF_3$ | 0 |
| I-24 | CN | 4-$OCH_3$ | $CF_3$ | 0 |
| I-25 | CN | 3-$CH_3$ | $CF_3$ | 0 |
| I-26 | $OCH_3$ | 4-F | $CF_3$ | 0 |
| I-27 | $OCH_2CH_3$ | 3-$CF_3$ | $CF_3$ | 0 |
| I-28 | $OCH_3$ | 3-$OCH_2CH=CH_2$ | $CF_3$ | 1 |
| I-29 | $OCH_3$ | 3-$OCH_2CH=CH_2$ | $CF_3$ | 0 |

(A) Figures preceding a hyphen symbol (-) represent the bonded position, whereas symbols following the hyphen symbol (-) represent the substituent and the number thereof when the substituents bond to 2 or more positions. For example, 4-$OCH_3$ in the Compound (I-10) means that methoxy bonds to the position 4, and 2,4-$F_2$ in the Compound (I-8) means that two atoms of fluorine bond respectively to the positions 2 and 4.

bonds to the position 4, and 2,4-$F_2$ in the Compound (I-8) means that two atoms of fluorine bond respectively to the positions 2 and 4.

The 2-(unsubstituted or substituted)(benzyloxy or phenoxy)-4-substituted-6-(meta-substituted phenoxy) pyridine of the formula (I) (Compound (I)) can be synthesized in accordance with the Reaction scheme I set forth in the following.

Reaction scheme I

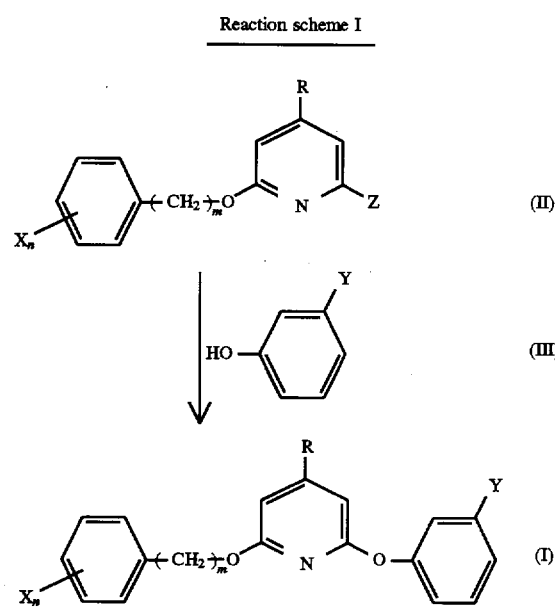

wherein R, X, Y, Z, m, and n are as defined above.

The 2-(unsubstituted or substituted) (benzyloxy or phenoxy)-4-substituted-6-halogenopyridine of the formula (II) may be synthesized in accordance with the Reaction scheme II.

Reaction scheme II

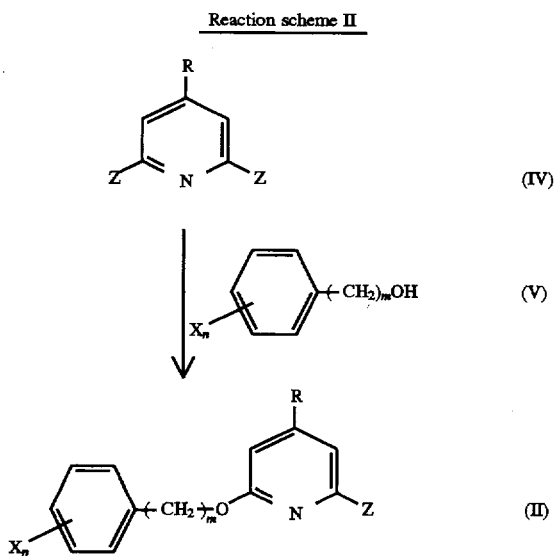

wherein R, X, Y, Z, m, and n are as defined above, and each Z in the formula (IV) may be identical or different.

Among the Compounds (I), those compounds wherein the substituent bonded to the position 2 is identical with the substituent bonded to the position 6 may be also synthesized in accordance with the reaction scheme III.

Reaction scheme III

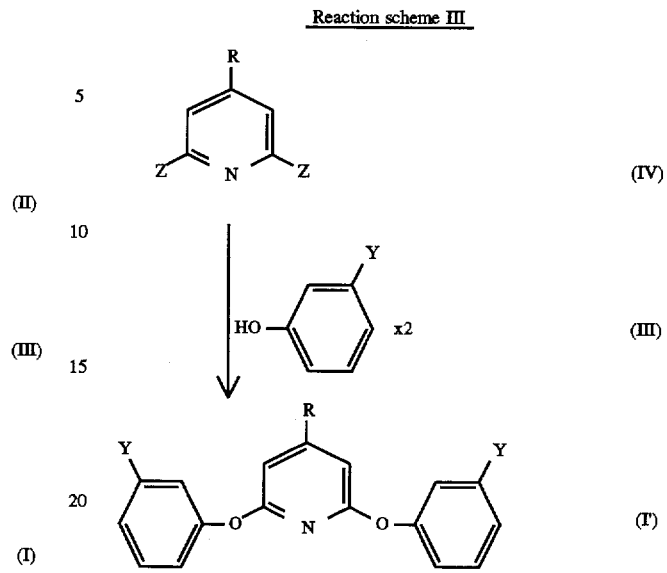

wherein R, Y, and Z are as defined above.

Examples of the unsubstituted or substituted benzyl alcohol or phenol of the formula (V) which may be used for the production of the Compounds (I) include the following.

Examples of the unsubstituted or substituted benzyl alcohol are as follows: benzyl alcohol, 2-chlorobenzyl alcohol, 3-chlorobenzyl alcohol, 4-chlorobenzyl alcohol, 2-fluorobenzyl alcohol, 3-fluorobenzyl alcohol, 4-fluorobenzyl alcohol, 4-methylbenzyl alcohol, 4-methoxybenzyl alcohol, 2,4-difluorobenzyl alcohol, 2,6-difluorobenzyl alcohol, 3,5-difluorobenzyl alcohol, 3-allkyloxybenzyl alcohol, and 3-(2-propynyl)oxybenzyl alcohol.

Examples of the unsubstituted or substituted phenol are as follows: phenol, 4-fluorophenol, 3-methylphenol, 4-methoxyphenol, 3-trifluoromethylphenol, 3-difluoromethoxyphenol, 3-trifluoromethoxyphenol, and 3-(trifluoromethylthio)phenol.

The meta-substituted phenol of the formula (III) includes meta-trifluoromethylphenol, meta-difluoromethoxyphenol, meta-trifluoromethoxyphenol, and meta-trifluoromethylthiophenol.

The unsubstituted or substituted benzyl alcohol of the formula (V) and the meta-substituted phenol of the formula (III) may be commercially available or may be easily obtained in accordance with existing techniques.

The 2,6-dihalogeno-4-substituted-pyridine of the formula (IV) (Compound (IV)) may also be commercially available or may be easily obtained in accordance with existing techniques.

For instance, 2,6-dichloro-4-cyanopyridine is the compound described in the publications such as Roczniki Chem. 1959, 33, 387 and the like. 2,6-Dichloro-4-methoxypyridine and 2,6-dibromo-4-methoxypyridine are described respectively in the J. Chem. Soc. B 1967, (8), 758 and Chem. Ber. 1989, 122(3), 589.

Further, it can be prepared by substituting a suitable group for nitro of 2,6-dichloro-4-nitropyridine described in EP 053306 A by the nucleophilic displacement using $C_1$–$C_4$ alkanol such as methyl alcohol, ethyl alcohol, or 1-methylethyl alcohol.

For both of the Reaction schemes (I) and (III), the Compound (IV) wherein the halogen represented by the symbol Z is chlorine, bromine, or iodine is preferably used.

According to the production process of the present invention, every reaction is advantageously conducted in a solvent or a mixture of solvents. Examples of the solvents which may be used in the production process of the present invention are set forth below:

aromatic hydrocarbons such as benzene, toluene, xylene, and methylnaphthalene;

aliphatic hydrocarbons such as petroleum ether, pentane, hexane, heptane, and methylcyclohexane;

halogenated hydrocarbons such as methylene chloride, chloroform, carbon tetrachloride, and chlorobenzene;

amides such as dimethylformamide, dimethylacetamide, and N-methyl-2-pyrrolidinone;

ethers such as diethyl ether, dimethoxyethane, diisopropyl ether, tetrahydrofuran, diglyme, and dioxane;

as well as others including carbon disulfide, acetonitrile, ethyl acetate, pyridine, dimethyl sulfoxide, hexamethylphosphoric amide, and the like.

When the production process of the present invention is carried out in the solvent, these solvents may be used alone or in combination of two or more. A mixture of the solvents incapable of forming a homogeneous phase may also be used. In this case, the reaction may suitably be conducted in the presence of a phase transfer catalyst such as a conventional quaternary ammonium salt or crown ether.

Since the production process of the present invention is based on nucleophilic displacement at the carbon atom on the pyridine ring, the reaction may preferably be conducted in the presence of a base. Further, copper(I) chloride, copper (I) bromide, and copper(I) iodide are preferably used with the base. Examples of the base are the basic compounds as follows:

alkaline metals such as lithium, sodium, and potassium, and alkaline earth metals such as magnesium;

alkaline metal alkoxides such as sodium methoxide, sodium ethoxide, and potassium t-butoxide;

alkaline metal hydrides such as sodium hydride and potassium hydride;

alkaline metal carbonates such as potassium carbonate, and sodium carbonate;

alkaline metal hydrogen carbonates such as sodium hydrogen carbonate and potassium hydrogen carbonate;

alkaline metal hydroxides such as sodium hydroxide and potassium hydroxide;

alkaline earth metal hydrides such as calcium hydride;

organic alkaline metal compounds. such as methyl lithium, ethyl lithium, n-butyl lithium, and phenyl lithium;

Grignard reagents such as methylmagnesium iodide, ethylmagnesium bromide, and n-butylmagnesium bromide;

organic copper compounds prepared from organic alkaline metal compounds or Grignard reagents and copper(I) salts; and alkaline metal amides such as lithium diisopropylamide.

The reaction conditions for each of the Reaction schemes I, II and III may be suitably selected and these reactions are usually conducted respectively at the temperature in the range of 1° to 200° C. for 0.5 to 30 hours, at the temperanure in the range of 1° to 180° C. for 0.5 to 10 hours and at the temperature in the range of 1° to 200° C. for 0.5 to 30 hours, if necessary, under pressurization.

Although the Compound (I) of the present invention may be applied as it is, it is generally applied after being formulated with an adjuvant into various forms of compositions such as powders, wettable powders, granules or emulsifiable concentrates.

When formulated, the composition usually contain one or more of the Compound (I) at an amount of 0.1 to 95% by weight, preferably 0.5 to 90% by weight, more preferably 2 to 70% by weight.

Among adjuvants including carriers(diluents) and surface active agents, examples of solid carriers are talc, kaolin, bentonite, diatomaceous earth, white carbon, clay, and the like. Examples of liquid diluents are water, xylene, toluene, chlorobenzene, cyclohexane, cyclohexanone, dimethylsulfoxide, dimethylformamide, alcohol, and the like. Surface active agents may be properly selected depending upon their effects, and suitable emulsifying agents include polyoxyethylene alkylaryl ether, polyoxyethylene sorbitan monolaurate, and the like. Suitable dispersing agents include lignin sulfonate, dibutylnaphthalene sulfonate, and the like. Suitable wetting agents include aikyl sulfonates, alkylphenyl sulfonates, and the like.

The above mentioned compositions include that which are to be applied as such, and those which are to be applied after being diluted to a proper concentration by using diluents such as water. In a diluted form, the Compound (I) is contained preferably at a concentration of 0.001 to 1.0% by weight. Application dose of the Compound (I) of the present invention is usually 0.01 to 10 kg/ha, preferably 0.05 to 5 kg/ha.

The concentrations and the application doses described above are varied depending on dosage forms, time of application, way of application, application sites, crops to be treated, and the like. Thus, modifications thereof are possible without being limited to the above defined range. Further, the Compound (I) of the present invention may be used in combination with other active ingredients such as fungicides, insecticides, acaricides and herbicides.

EXAMPLES

The 2-(unsubstituted or substituted benzyloxy or phenoxy)-4-substituted-6-(meta-substituted phenoxy) pyridine of the present invention, production processes and use thereof will be more specifically described by way of synthesis examples, formulation examples and test examples set forth in the following.

It will be also understood that the present invention should be considered as not limited to these examples without departing from the scopes thereof.

Synthesis Example 1

Synthesis of 2-benzyloxy-4-methoxy-6-(meta-trifluoromethylphenoxy)pyridine (I-1)

(1) Synthesis of an Intermediate, 2,6-dichloro-4-methoxypyridine

To a tetrahydrofuran solution containing methanol (0.37 g, 0.0104×1.1 mol), sodium hydride (0.44 g (ca. 60% in mineral oil), 0.0104×1.05 mol) was added, then 2,6-dichloro-4-nitropyridine (2.00. g, 0.0104 mol) was added thereto and the resultant solution was stirred for about 2 hours at room temperature. After it was confirmed that there was no bubbling with the addition of methanol (1.0 g, 0.0355×0.9 mol), the resultant solution was stirred for about another 1 hour. After the reaction solution was partitioned between ethyl acetate and water, the obtained organic layer was washed successively with aqueous saturated sodium hydrogen carbonate and aqueous saturated sodium chloride, dried over anhydrous sodium sulfate and thereafter concentrated to obtain the substantially pure end product.

Yield: 1.63 g (88%). Solid. Melting point: 94° to 96° C. $^1$H-NMR (60 MHz, CDCl$_3$, δ): 3.79(3H, s), 6.70(2H, s).

(2) Synthesis of an Intermediate, 2-benzyloxy-6-chloro-4-methoxypyridine

To a tetrahydrofuran solution containing benzyl alcohol (0.58 g, 0.0045×1.2 mol), sodium hydride (0.19 g (ca. 60% in mineral oil), 0.0045×1.05 mol) was added.

Then, 2,6-dichloro-4-methoxypyridine (0.8 g, 0.0045 mol) was added thereto and the resultant solution was refluxed for about 1 hour. The reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The residue was purified on a silica gel column to obtain the end product.

Yield: 1.23 g (86%). Oily product. $^1$H-NMR (60 MHz, CDCl$_3$, δ): 3.68(3H, s), 5.25(2H, s), 6.07(1H, d, J=2.0 Hz), 6.44(1H, d, J=2.0 Hz), 7.0–7.6(5H, complex).

(3) Synthesis of 2-benzyloxy-4-methoxy-6-(meta-trifluoromethylphenoxy)pyridine from the Intermediate To a dimethylformamide solution containing meta-trifluoromethyl phenol (1.29 g, 0.0020×4.0 mol), sodium hydride (0.32 q (ca. 60% in mineral oil), 0.0020×4.0 mol) was added.

Then, 2-benzyloxy-6-chloro-4-methoxypyridine (0.5 g, 0.0020 mol) and CuI (0.19 g, 0.0020×0.5 mol) were successively added thereto and the resultant solution was refluxed for about 4 hours. The reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The residue was purified on a silica gel column to obtain the end product.

Yield: 0.29 g (39%). Solid. Melting point: 46° to 48° C. $^1$H-NMR (60 MHz, CDCl$_3$, δ): 3.69(3H, s), 5.04(2H, s), 5.96(2H, s), 7.0–7.6(9H, complex).

Synthesis Example 2

Synthesis of 2-benzyloxy-4-methoxy-6-(meta-trifluoromethoxyphenoxy)pyridine (I-2)

(1) Synthesis of an Intermediate, 2,6-dibromo-4-methoxypyridine

Sodium hydride (1.49 g (ca.60% in mineral oil), 0.0355×1.05 mol) was washed with hexane and suspended in tetrahydrofuran, and methanol (1.70 g, 0.0355×1.5 mol) was added thereto. Then, 2,6-dibromo-4-nitropyridine (10.00 g, 0.0355 mol) was added thereto and the resultant solution was stirred for about 1 hour at room temperature.

Additional sodium hydride (0.2 g (Ca.60% in mineral oil), 0.0355×0.14 mol) was added, then the resultant solution was stirred for about 1 hour. After it was confirmed that there was no bubbling with the addition of methanol (1.0 g, 0.0355×0.9 mol), the reaction solution was partitioned between ethyl acetate and aqueous saturated sodium hydrogen carbonate. The obtained organic layer was washed with aqueous saturated sodium chloride, dried over anhydrous sodium sulfate and thereafter concentrated to obtain the end product.

Yield: 9.27 g (98%). Solid. Melting point: 131° to 133° C. $^1$H-NMR (60 MHz, CDCl$_3$, δ): 3.79(3H, s), 6.89(2H, s).

(2) Syntnesis of an Intermediate, 2-benzyloxy-6-bromo-4-methoxypyridine

To a tetrahydrofuran solution containing benzyl alcohol (1.7 g, 0.0131×1.2 mol), sodium hydride (0.55 g (ca.60% in mineral oil), 0.0131×1.05 mol) was added.

Then, 2,6-dibromo-4-methoxypyridine (3.5 g, 0.0131 mol) was added thereto and the resultant solution was refluxed for about 2 hours. The reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end product was obtained.

Yield: 3.35 g (87%). Oily product. $^1$H-NMR (60 MHz, CDCl$_3$, δ): 3.63(3H, s), 5.25(2H, s), 6.04(1H, d, J=2.0 Hz), 6.53(1H,d, J=2.0 Hz), 7.0–7.5(5H, complex).

(3) Synthesis of 2-benzyloxy-4-methoxy-6-(meta-trifluoromethoxyphenoxy)pyridine from the Intermediate To a dimethylformamide solution containing meta-trifluoromethoxy phenol (0.52 g, 0.0013×2.2 mol), sodium hydride (0.11 g (ca.60% in mineral oil), 0.0013×2.1 mol) was added.

Then, 2-benzyloxy-6-bromo-4-methoxypyridine (0.39 g, 0.0013 mol) and CuI (0.06 g, 0.0013×0.5 mol) were successively added thereto and the resultant solution was stirred for about 21 hours at the temperature of about 110° to 120° C. The reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end product was obtained.

Yield: 0.24 g (46%). Oily product. $^1$H-NMR (60 MHz, CDCl$_3$, δ): 3.67(3H, s), 5.04(2H, s), 5.93(2H, s), 6.7–7.4 (9H, complex).

Synthesis Example 3

Synthesis of 2-benzyloxy-4-cyano-6-(meta-trifluoromethylphenoxy)pyridine (I-3)

(1) Synthesis of an Intermediate, 2-benzyloxy-6-chloro-4-cyanopyridine

Sodium hydride (0.24 g (ca.60% in mineral oil), 0.006×1.0 mol) was suspended in 20 ml of N-methyl-2-pyrrolidinone, and benzyl alcohol (0.65 g, 0.006×1.0 mol) was added thereto and the resultant solution was stirred for about 30 minutes at room temperature.

The obtained mixture was cooled with iced water to about 4° C., then 4-cyano-2,6-dichloropyridine (1.04 g, 0.006 mol) was added thereto, and the resultant solution was stirred for about 1.5 hour while cooling with iced water.

After the stirring was continued for about another 1.5 hour at room temperature, the reaction solution was partitioned between ethyl acetate and water. The obtained organic layer was washed with aqueous saturated sodium chloride, dried over anhydrous sodium sulfate and thereafter concentrated. The concentrate was purified on a silica gel column to obtain the end product.

Yield: 0.94 g (64%). Oily product. $^1$H-NMR (60 MHz, CDCl$_3$, δ): 5.33(2H, s), 6.88(1H, s), 7.05(1H, s), 7.35(5H, s).

(2) Synthesis of 2-benzyloxy-4-cyano-6-(meta-trifluoromethylphenoxy)pyridine from the Intermediate 2-Benzyloxy-6-chloro-4-cyanopyridine (0.8 g, 0.0033 mol) and meta-trifluoromethyl phenol (0.58 g, 0.0033×1.1 mol) were dissolved in 20 ml of N-methyl-pyrrolidinone, and anhydrous potassium carbonate (0.5 g, 0.0033×1.1 mol) was added thereto and the resultant solution was stirred for about 2.5 hours at about 100° C.

The reaction solution was partitioned between ethyl acetate and water. The obtained organic layer was washed with aqueous saturated sodium chloride, dried over anhydrous sodium sulfate and thereafter concentrated.

The concentrate was purified on a silica gel column, then recrystallized from a small amount of n-hexane to obtain the end product.

Yield: 0.89 g (74%). Solid. Melting point 75° to 76° C. $^1$H-NMR (60 MHz, CDCl$_3$, δ): 5.03(2H, s), 6.6–6.7(2, bs), 6.8–7.6(9H, complex).

Synthesis Example 4

Synthesis of 4-methoxy-2,6-di(meta-trifluoromethylphenoxy)-pyridine (I-18)

To meta-trifluoromethyl phenol (2.5 g, 0.0028×5.5 mol), 15 ml of dimethylformamide was added, followed by the addition of sodium hydride (0.45 g (ca.60% in mineral oil), 0.0028×4.0 mol) and CuI (0.25 g, 0.0028×0.47 mol). To thus formed mixture was added 2,6-dichloro-4-methoxy-pyridine (0.5 g, 0.0028 mol), and the resultant solution was refluxed for about 8 hours.

Then the reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and a low-boiling material which was difficult to separate was distilled off by using a tubular oven, whereby the end product was obtained.

Yield: 0.13 g (11%). Oily product. $^1$H-NMR (60 MHz, CDCl$_3$, δ): 3.76(3H, s), 6.07(2H, s), 6.7–7.4 (8H, complex).

Synthesis Example 5

Synthesis of 4-methoxy-2-phenoxy-6-(meta-trifluoromethoxyphenoxy)pyridine (I-22)

(1) Synthesis of an Intermediate, 2-bromo-4-methoxy-6-phenoxypyridine

To a dimethylformamide solution containing phenol (0.58 g, 0.0056×1.1 mol), sodium hydride (0.24 g (ca.60% in mineral oil)., 0.0056×1.07 mol) was added.

Then, 2,6-dibromo-4-methoxypyridine (1.5 g, 0.0056 mol) was added thereto and the resultant solution was stirred for about 2 hours at about 110° C.

Thereafter, the reaction solution was partitioned between hexane and aqueous saturated sodium hydrogen carbonate. The obtained organic layer was washed with aqueous saturated sodium chloride, dried over anhydrous sodium sulfate and thereafter concentrated. The concentrate was purified on a silica gel column, then crystallized from hexane to obtain the end product.

Yield: 0.83 g (53%). Oily product. $^1$H-NMR (60 MHz, CDCl$_3$, δ): 3.67(3H, s), 6.12(1H, d, J=2.0 Hz), 6.66(1H, d, J=2.0 Hz), 6.8–7.5(5H, complex).

(2) Synthesis of 4-methoxy-2-phenoxy-6-(meta-trifluoromethoxyphenoxy)pyridine from the Intermediate To a dimethylformamide solution containing meta-trifluoromethoxy phenol (0.47 g, 0.0026×1.1 mol), sodium hydride (0.11 g, (ca.60% in mineral oil), 0.0026×1.06 mol) was added.

Then, 2-bromo-4-methoxy-6-phenoxypyridine (0.73 g, 0.0026 mol) and CuCl (0.13 g, 0.0026×0.5 mol) were successively added thereto and the resultant solution was stirred for about 8 hours at about 120° C.

Additional amounts of meta-trifluoromethoxy phenol (0.47 g, 0.0026×1.1 mol) and sodium hydride (0.11 g, (ca.60% in mineral oil), 0.0026×1.06 mol) were added thereto. After the resultant solution was stirred for about another 8 hours at about 120° C., the reaction solution was partitioned between hexane and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end product was obtained.

Yield: 0.66 g (70%). Oily product. $^1$H-NMR (60 MHz, CDCl$_3$, δ): 3.68(3H, s), 5.8–6.2(2H, complex), 6.7–7.5 (9H, complex)

Synthesis Example 6

Synthesis of 4-cyano-2,6-di(meta-trifluoromethylphenoxy)-pyridine (I-23)

Sodium hydride (0.31 g (ca. 60% in mineral oil), 0.0035×2.2 mol) was suspended in 20 ml of N-methyl-2-pyrrolidinone, then meta-trifluoromethyl phenol (1.24 g, 0.0035×2.2 mol) was added thereto, and the resultant solution was heated to about 60° C. and stirred for several minutes. After allowed to cool to room temperature, to the reaction solution was added 4-cyano-2,6-dichloropyridine (0.60 g, 0.0035 mol), and then the mixture was allowed to react for 1 hour at about 90° C.

Then, the reaction solution was partitioned between ethyl acetate and water. The obtained organic layer was washed with aqueous saturated sodium chloride, dried over anhydrous sodium sulfate and thereafter concentrated. The concentrate was purified on a silica gel column, then recrystallized from a small amount of n-hexane to obtain the end product.

Yield: 0.91 g (62%). Solid. Melting point: 51° to 52° C. $^1$H-NMR (60 MHz, CDCl$_3$, δ): 6.80(2H, s), 6.8–7.5(8H, complex).

Synthesis Example 7

Synthesis of 4-cyano-2-(para-methoxyphenoxy)-6-(meta-trifluoromethylphenoxy)pyridine (I-24)

(1) Synthesis of an Intermediate, 2-chloro-4-cyano-6-(para-methoxyphenoxy)pyridine To a tetrahydrofuran solution containing para-methoxy phenol (1.18 g, 0.00867×1.1 mol), sodium hydride (0.36 g (ca.60% in mineral oil), 0.00867×1.04 mol) was added.

Then, 4-cyano-2,6-dichloropyridine (1.5 g, 0.00867 mol) was added thereto and the resultant solution was refluxed for about 2-hours. The reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column to obtain the end product.

Yield: 1.73 g (77%). Solid. Melting point: 99° to 101° C. $^1$H-NMR (60 MHz, CDCl$_3$, δ): 3.71(3H, s), 6.5–7.3(6H, complex).

(2) Synthesis of 4-cyano-2-(para-methoxyphenoxy)-6-(meta-trifluoromethoxyphenoxy)pyridine To a dimethylformamide solution containing meta-trifluoromethoxyphenol (0.52 g, 0.0027×1.2 mol), sodium hydride (0.12 g, (ca.60% in mineral oil), 0.0027×1.1 mol) was added.

Then, 2-chloro-4-cyano-6-(para-methoxyphenoxy) pyridine (0.70 g, 0.0027 mol) and CuCl (0.13 g, 0.0027×0.5 mol) were successively added thereto and the resultant solution was stirred for about 2 hours at about 120° C.

The reaction solution was partitioned between hexane and aqueous saturated sodium hydrogen carbonate. The obtained organic layer was washed with aqueous saturated sodium chloride, dried over anhydrous sodium sulfate and thereafter concentrated. The concentrate was purified on a silica gel column and the starting material which was difficult to separate was distilled off by using a tubular oven, whereby the end product was obtained.

Yield: 0.78 g (75%). Oily product. $^1$H-NMR (60 MHz, CDCl$_3$, δ): 3.66(3H, s), 6.4–7.5(10H, complex).

Synthesis Example 8

Synthesis of 4-ethoxy-2,6-di-(meta-trifluofomethylphenoxy)-pyridine (I-27)

To meta-trifluoromethyl phenol (1.94 g, 0.00285×4.2 mol), dimethylformamide was added. Then, sodium hydride (0.46 g (ca.60% in mineral oil), 0.00285×4.0 mol) and CuCl (0.28 g, 0.00285×1.00 mol) were successively added thereto. To the mixture thus formed, 4-ethoxy-2,6-dibromopyridine (0.8 g, 0.00285 mol) was added and the resultant solution was allowed to react for about 6 hours at the temperature of about 110° to 120° C.

Then, the reaction solution was partitioned between ethyl acetate and aqueous saturated sodium hydrogen carbonate. The obtained organic layer was washed with aqueous saturated sodium chloride, dried over anhydrous sodium sulfate and thereafter concentrated. The concentrate was purified on a silica gel column and a low-boiling material was distilled off by using a tubular oven, whereby the end product was obtained.

Yield: 1.05 g (83%). Oily product. $^1$H-NMR (60 MHz, CDCl$_3$, δ): 1.38(3H,t, J=6.9 Hz), 4.00(2H, q, J=6.9 Hz), 6.61(2H, s), 6.9–7.5(8H, complex).

The other compounds shown in the Table 1 were also synthesized in a similar manner to that described in any of the above Synthesis examples 1 to 8. Properties and NMR data of the obtained compounds are shown in the Table 2.

TABLE 2

| No. | Property | $^1$H-NMR 60 MHz, CDCl$_3$, δ |
|---|---|---|
| I-4 | Oily | 3.69(3H,s), 5.02(2H,s), 5.93(2H,s), 7.0–7.6(9H,complex). |
| I-5 | Oily | 3.70(3H,s), 4.95(2H,s), 5.93(2H,s), 6.7–7.5(8H,complex). |
| I-6 | Oily | 3.72(3H,s), 4.98(2H,s), 5.95(2H,s), 6.8–7.5(8H,complex). |
| I-7 | Oily | 3.72(3H,s), 5.13(2H,s), 5.99(2H,s), 6.9–7.5(8H,complex). |
| I-8 | Oily | 3.72(3H,s), 5.00(2H,s), 5.94(2H,s), 6.4–7.5(7H,complex). |
| I-9 | Oily | 3.69(3H,s), 4.95(2H,s), 5.92(2H,s), 6.5–7.5(8H,complex). |
| I-10 | Oily | 3.66(6H,s), 4.92(2H,s), 5.89(2H,s), 6.4–7.5(8H,complex). |
| I-11 | Solid m.p. 57–60° C. | 2.23(3H,s), 3.63(3H,s), 4.93(2H,s), 5.90 (2H,s), 6.6–7.5(8H,complex). |
| I-12 | Oily | 3.69(3H,s), 5.09(2H,s), 5.94(2H,s), 6.8–7.9(8H,complex). |
| I-13 | Oily | 3.70(3H,s), 5.01(2H,s), 5.98(2H,s), 6.5–7.5(8H,complex). |
| I-14 | Oily | 3.70(3H,s), 5.11(2H,s), 5.94(2H,s), 6.4–7.5 (7H, complex). |
| I-15 | Oily | 3.71(3H,s), 4.95(2H,s), 5.95(2H,s), 6.2–7.5(7H,complex). |
| I-16 | Oily | 1.33(3H,t, J=7.1Hz), 3.62(2H,q,J=7.1Hz), 5.04(2H,s), 5.93(2H,s), 7.0–7.5(9H,complex). |
| I-17 | Oily | 3.62(3H,s), 5.03(2H,s), 5.90(2H,s), 6.33(1H,t,J=73Hz), 6.6–7.4(9H,complex). |
| I-19 | Oily | 3.74(3H,s), 6.06(2H,s), 6.8–7.5(8H,complex). |
| I-20 | Oily | 3.73(3H,s), 6.04(2H,s), 6.5–7.4(8H,complex). |
| I-21 | Oily | 3.72(3H,s), 6.04(2H,s), 6.29(1H,t,J=73Hz), 6.5–7.4(8H,complex). |
| I-25 | Oily | 2.21(3H,s), 6.5–7.5(10H,complex). |
| I-26 | Oily | 3.68(3H,s), 5.8–6.1(2H,complex), 6.5–7.5(8H,complex). |
| I-28 | Oily | 3.69(3H,s), 4.2–4.6(2H,complex), 5.01(2H,s), 4.9–5.6(2H,complex), 5.6–6.4(1H,multiplet), 5.95(2H,s), 6.7–7.5(8H,complex). |
| I-29 | Oily | 3.69(3H,s), 4.2–4.6(2H,complex), 5.0–5.6(2H,complex), 5.6–6.3(3H,complex), 6.3–6.7(3H,complex), 6.7–7.4(5H,complex). |

Formulation examples and test examples are hereinafter described. Kinds of carriers (diluents) and additives to be used, as well as mixing ratios thereof and active ingredient contents therein may be modified in a broad range.

In each of the formulation examples, the term "parts" is "parts by weight" if otherwise noticed.

Formulation Example 1 (wettable powder)

| Compound No. I-3 | 50 parts |
|---|---|
| Lignin sulfonate | 5 parts |
| Alkyl sulfonate | 3 parts |
| Diatomaceous earth | 42 parts |

The above materials were mixed together and ground finely to form a wettable powder. It may be applied after diluted with water.

Formulation Example 2 (emulsifiable concentrate)

| Compound No. I-1 | 25 parts |
|---|---|
| Xylene | 65 parts |
| Polyoxyethylene alkylaryl ether | 10 parts |

The above materials were homogeneously mixed to form an emulsifiabie concentrate. It may be applied after diluted with water.

Formulation Example 3 (granule)

| Compound No. I-2 | 8 parts |
|---|---|
| Bentonite | 40 parts |
| Clay | 45 parts |
| Lignin sulfonate | 7 parts |

The above materials were homogeneously mixed, blended with water and processed into a granular form with an extrusion granulator to give granules.

Test Example 1 (Weed control test by foliage and soil treatments)

A wettable powder of each test compound was prepared as described in the Formulation Example 1 and suspended in water to a predetermined concentration. Thus prepared herbicidal solution was applied at an active ingredient rate of 5 g/10 a onto the soil and the foliage of each plant grown to the 1 to 2 leaf stage. The tested plants were pot-cultivated redroot pigweed (*Amaranthus retroflexus*), wild mustard (*Sinapis arvensis*), common chickweed (*Stellaria media*), sicklepod (*Cassia obtusifolia*), black nightshade (*Solanum nigrum*), velvetleaf (*Abutilon theophrasti*), field bindweed (*Convolvulus arvensis*), wild chamomile (*Matricaria chamomilla*), green foxtail (*Setaria viridis*), barnyard grass (*Echinochloa frumentaceum*), and henry crabgrass (*Digitaria adscendens*).

On the 14th day after the application, weed control effects were evaluated by the following criterion.

Evaluation rating:

1: less than 20% of weedkilling;
2: 20% to less than 40% of weedkilling;
3: 40% to less than 60% of weedkilling;
4: 60% to less than 80% of weedkilling;
5: more than 80% of weedkilling.

The results are shown in the Table 3. In the test example, the compounds (A) to (D) which were disclosed in EP 572093 A and the compound (E) (Registry Number 153564-12-6 in Chem. Abstr.) which was not described in the publication but abstracted in the Chemical Abstracts [120, P 191543h(1994)] as a compound disclosed in the publication were also tested as comparative compounds:

(A) 2,6-di(meta-trifluromethylphenoxy)pyridine;

(B) 2,6-di(meta-trifluromethylphenoxy)-4-methylmercaptopyridine;

(C) 2,6-di(meta-trifluromethylphenoxy)-4-methylpyridine;

(D) 2-benzyloxy-6-(meta-trifluromethylphenoxy)pyridine; and (E) 4-chloro-2,6-di(meta-trifluromethylphenoxy)pyridine.

(This compound is thought a position isomer of the compound of Ex. No. 14 in EP 572093 A, but more closely related to the present invention concerning the binding position of pyridine.)

TABLE 3

| No. | AR | SA | SM | CO | SN | AT | CA | MC | SV | EF | DA |
|---|---|---|---|---|---|---|---|---|---|---|---|
| (A) | 2 | 1 | 1 | 1 | 1 | 1 | 1 | 1 | 1 | 1 | 1 |
| (B) | 2 | 4 | 1 | 1 | 3 | 1 | 3 | 1 | 1 | 1 | 1 |
| (C) | 5 | 5 | 4 | 5 | 5 | 3 | 3 | 2 | 2 | 1 | 4 |
| (D) | 4 | 5 | 5 | 1 | 5 | 1 | 1 | 2 | 1 | 1 | 4 |
| (E) | 5 | 5 | 4 | 3 | 5 | 3 | 4 | 1 | 1 | 1 | 4 |
| I-1 | 5 | 5 | 5 | 5 | 5 | 5 | 5 | 5 | 4 | 1 | 5 |
| I-2 | 5 | 5 | 5 | 5 | 5 | 5 | 5 | 5 | 5 | 1 | 4 |
| I-3 | 5 | 5 | 5 | 5 | 5 | 5 | 5 | 5 | 2 | 2 | 5 |
| I-6 | 5 | 5 | 5 | 4 | 5 | 5 | 4 | 3 | 3 | 1 | 4 |
| I-7 | 5 | 5 | 5 | 4 | 5 | 3 | 4 | 4 | 3 | 2 | 5 |
| I-8 | 5 | 5 | 5 | 5 | 5 | 4 | 4 | 5 | 4 | 2 | 5 |
| I-9 | 5 | 5 | 5 | 5 | 5 | 5 | 5 | 4 | 4 | 3 | 5 |
| I-18 | 5 | 5 | 5 | 5 | 5 | 4 | 5 | 4 | 2 | 2 | 5 |
| I-23 | 5 | 5 | 5 | 5 | 5 | 5 | 5 | 3 | 3 | 2 | 5 |

(A): AR: Amaranthus retroflexus; SA: Sinapis arvensis; SM: Stellaria media; CO: Cassia obtusifolia; SN: Solanum nigrum; AT: Abutilon theophrasti; CA: Convolvulus arvensis; MC: Matricaria chamomilla; SV: Setaria viridis; EF: Echinochloa frumentaceum; and DA: Digitaria adscendens.

What is claimed is:

1. A 2-(unsubstituted or substituted) (benzyloxy or phenoxy)-4-substituted-6-(meta-substituted phenoxy) pyridine represented by the formula (I):

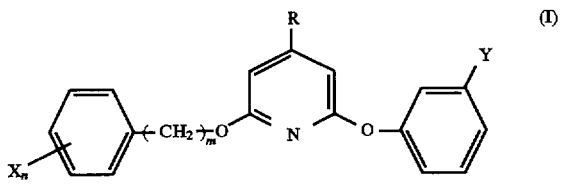

wherein R represents $C_1$–$C_4$ alkoxy or cyano;

each X, which may be identical or different if n is greater than 1, represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5.

2. A compound according to claim 1, wherein R represents methoxy or cyano and m is 0 or 1.

3. A process for producing a 2-(unsubstituted or substituted)(benzyloxy or phenoxy)-4-substituted-6-(meta-substituted phenoxy)pyridine of the formula (I):

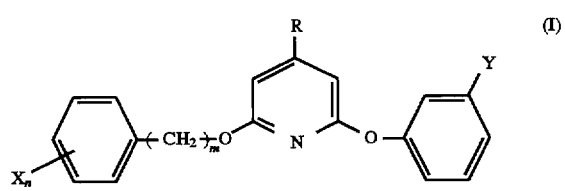

wherein R represents $C_1$–$C_4$ alkoxy or cyano;

each X, which may be identical or different if n is greater than 1, represents a halogen, $C_1$–$C_4$ alkoxy, $C_1$–$C_4$ alkyl $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5, which process comprises reacting a 2-(unsubstituted or substituted)(benzyloxy or phenoxy)-4-substituted-6-halogenopyridine of the formula (II):

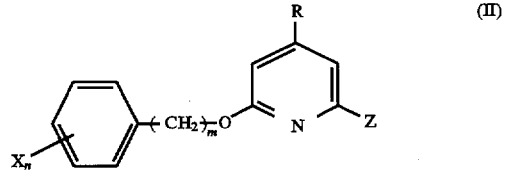

wherein R, X, m, and n are as defined above; and

Z represents a halogen, with a meta-substituted phenol of the formula (III):

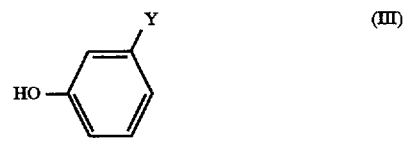

wherein Y is as defined above.

4. A process for producing a 2,6-di(meta-substituted phenoxy)-4-substituted-pyridine of the formula (I'):

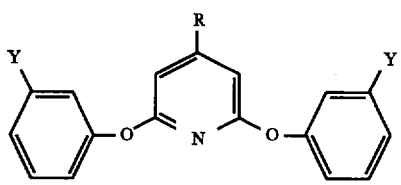
(I')

wherein R represents $C_1$–$C_4$ alkoxy or cyano; and

Y represents trifluoromethyl, difluoromethoxy, trifluoromethoxy, or trifluoromethylthio, which process comprises reacting a 2,6-dihalogeno-4-substituted-pyridine of the formula (IV):

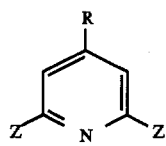
(IV)

wherein R is as defined above; and Z represents a halogen, with a meta-substituted phenol of the formula (III):

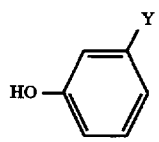
(III)

wherein Y is as defined above.

5. A herbicidal composition comprising a 2-(unsubstituted or substituted) (benzyloxy or phenoxy)-4-substituted-6-(meta-substituted phenoxy)pyridine of the formula (I):

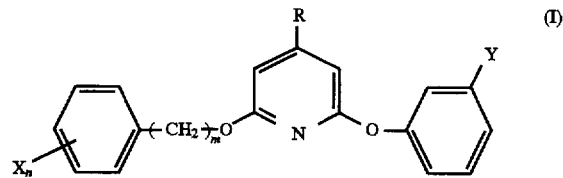
(I)

wherein R represents $C_1$–$C_4$ alkoxy or cyano;

each X, which may be identical or different if n is greater than 1 represents a halogen, $C_1$–$C_4$ alkoxy, $C_1$–$C_4$ alkyl, $C_1$–$C_4$ haloalkoxy, $C_1$–$C_4$ haloalkyl, $C_1$–$C_4$ haloalkylthio, $C_3$–$C_5$ alkenyloxy, or $C_3$–$C_5$ alkynyloxy;

Y represents trifluoromethyl, difluoromethoxy, trifluoromethoxy, or trifluoromethylthio;

m represents an integer of 0 or 1; and n represents an integer of 0 to 5, and an adjuvant.

6. A herbicidal composition according to claim 5, wherein R represents methoxy or cyano and m is 0 or 1.

* * * * *